(12) United States Patent
Zhang et al.

(10) Patent No.: US 10,736,695 B2
(45) Date of Patent: Aug. 11, 2020

(54) VISUAL FRACTIONAL LASER INSTRUMENT

(71) Applicant: ZWXG (BEIJING) TECHNOLOGY CO., LTD, Beijing (CN)

(72) Inventors: Kefei Zhang, Beijing (CN); Hongwei Wang, Beijing (CN); Yu Zhang, Changchun (CN); Shenghua Zheng, Beijing (CN); Ning Bao, Beijing (CN); Hongkui Wang, Ordos (CN); Hong Zheng, Hohhot (CN); Yuguan Zhang, Beijing (CN); Rong Zheng, Hohhot (CN); Jian Zhao, Beijing (CN); Heyi Zhang, Beijing (CN)

(73) Assignee: ZWXG (BEIJING) TECHNOLOGY CO., LTD, Beijing (CN)

( * ) Notice: Subject to any disclaimer, the term of this patent is extended or adjusted under 35 U.S.C. 154(b) by 127 days.

(21) Appl. No.: 15/566,185

(22) PCT Filed: Mar. 1, 2016

(86) PCT No.: PCT/CN2016/075197
§ 371 (c)(1),
(2) Date: Oct. 12, 2017

(87) PCT Pub. No.: WO2016/184215
PCT Pub. Date: Nov. 24, 2016

(65) Prior Publication Data
US 2018/0092694 A1  Apr. 5, 2018

(30) Foreign Application Priority Data
May 20, 2015  (CN) .......................... 2015 1 0259525

(51) Int. Cl.
 A61C 3/00    (2006.01)
 A61B 18/20   (2006.01)
 A61B 18/00   (2006.01)

(52) U.S. Cl.
 CPC .. *A61B 18/201* (2013.01); *A61B 2018/00559* (2013.01); *A61B 2018/00982* (2013.01);
(Continued)

(58) Field of Classification Search
CPC combination set(s) only.
See application file for complete search history.

(56) References Cited

U.S. PATENT DOCUMENTS 3,865,113 A * 2/1975 Sharon ................ A61B 18/201
                                                      606/18
5,743,902 A * 4/1998 Trost .................... A61B 18/203
                                                      606/11
(Continued)

FOREIGN PATENT DOCUMENTS

CN     103800083 B   *  4/2017   ............... A61C 3/00
WO     WO-9622741 A1 *  8/1996   ........... A61B 18/203
WO     WO-2011032165 A2 * 3/2011 ............. A61B 18/24

OTHER PUBLICATIONS

Google translation of CN 103800083, Wang et al. Mlni-automatic cutting apparatus an intraoral dental preparation 2013 (Year: 2013).*

*Primary Examiner* — Michael W Kahelin
*Assistant Examiner* — Shirley X Jian
(74) *Attorney, Agent, or Firm* — Lewis Roca Rothgerber Christie LLP

(57) ABSTRACT

The present invention provides a visual fractional laser instrument, which comprises: an positioning cannula, the positioning cannula being a hollow tube with openings at both ends so as to locate a lesion site and define a path of the laser; a beam combiner component, the beam combiner component being a hollow tube with openings at both ends,
(Continued)

and a side opening is provided on a side of the beam combiner component, wherein one end of the beam combiner component is connected to one end of the positioning cannula; a camera connected to the beam combiner component by the side opening to image the lesion site; a laser scanning component connected to another end of the beam combiner component for generating a laser beam used to scan the lesion site according to the image of the lesion site; and a control system connected to the laser scanning component and the camera, respectively. The visual fractional laser instrument is simple in operation, and the controlled laser beam automatically scans along a preset path and quickly burns castration pathological sites, thereby reducing operation time and surgeon workload, and increasing treatment efficiency and success rate.

8 Claims, 1 Drawing Sheet

(52) U.S. Cl.
CPC ............... *A61B 2018/2005* (2013.01); *A61B 2018/20355* (2017.05); *A61B 2018/20361* (2017.05)

(56) References Cited

U.S. PATENT DOCUMENTS

| | | | | |
|---|---|---|---|---|
| 5,846,182 | A * | 12/1998 | Wolcott | A61B 1/00135 600/114 |
| 5,864,393 | A * | 1/1999 | Maris | G01L 1/241 356/28 |
| 5,999,687 | A * | 12/1999 | Abraham | A61C 1/0046 385/33 |
| 7,951,139 | B2 * | 5/2011 | Assa | A61B 18/22 606/19 |
| 8,288,679 | B2 * | 10/2012 | Unrath | B23K 26/0648 219/121.67 |
| 8,496,579 | B2 * | 7/2013 | Koenig | A61B 1/00172 600/160 |
| 8,764,737 | B2 * | 7/2014 | Kurtz | A61F 9/00825 606/4 |
| 9,044,303 | B2 * | 6/2015 | Kurtz | A61F 9/00825 |
| 9,480,599 | B2 * | 11/2016 | Degani | A61B 3/13 |
| 10,111,779 | B2 * | 10/2018 | Degani | A61B 3/13 |
| 2006/0241572 | A1 * | 10/2006 | Zhou | A61B 8/12 606/7 |
| 2007/0042315 | A1 * | 2/2007 | Boutoussov | A61B 1/00163 433/29 |
| 2008/0081950 | A1 * | 4/2008 | Koenig | A61B 1/00172 600/160 |
| 2009/0187176 | A1 * | 7/2009 | Assa | A61B 18/22 606/17 |
| 2010/0100085 | A1 * | 4/2010 | Lewinsky | A61B 18/201 606/16 |
| 2010/0301024 | A1 * | 12/2010 | Unrath | B23K 26/0648 219/121.67 |
| 2011/0189628 | A1 * | 8/2011 | Monty | A61C 1/0046 433/29 |
| 2012/0116372 | A1 * | 5/2012 | Degani | A61B 3/13 606/4 |
| 2016/0322777 | A1 * | 11/2016 | Zediker | H01S 5/4012 |
| 2017/0014271 | A1 * | 1/2017 | Degani | A61B 3/13 |

* cited by examiner

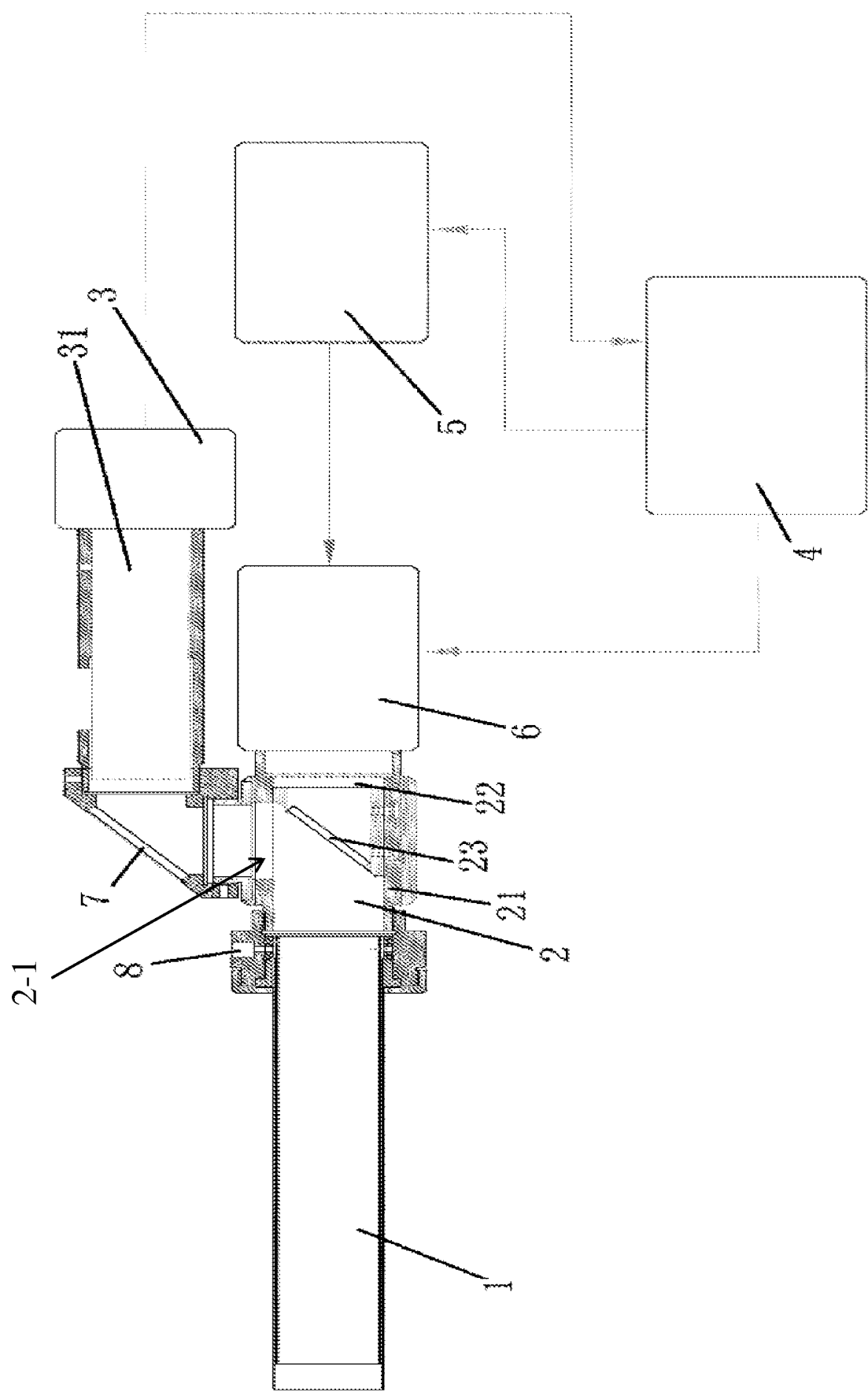

VISUAL FRACTIONAL LASER INSTRUMENT

CROSS-REFERENCE TO RELATED APPLICATION(S)

This application is a National Phase Patent Application of, and claims priority to and the benefit of International Patent Application Number PCT/CN2016/075197, filed on Mar. 1, 2016, which claims priority of CN Patent Application 201510259525.1, filed May 20, 2015. The entire contents of both of which are incorporated herein by reference.

FIELD OF THE INVENTION

The present invention generally relates to laser treatment field, and more particularly to a visual fractional laser instrument.

BACKGROUND

Cervical disease refers to a variety of lesions in the cervical region, including inflammation, injury, tumor, precancerous lesions, and the same, which is a female common disease. The treatment of chronic cervical inflammatory disorders mainly include Philip knife treatment and $CO_2$ laser treatment at present.

Philip knife, also known as high-frequency electric wave knife, uses directional radio frequency transmission technology. The radio frequency energy can directly stimulate the liquid polar molecules in the organization and produce plasma oscillation, which makes molecular bond break and further achieves the effect of fine minimally invasive treatment.

$CO_2$ laser targets at water. When the diameter of the laser beam is adjusted to hundreds of microns, the laser beam can penetrate cuticle tissue and enter dermal tissue at a certain energy density. Because this type of laser has highly water absorption, the organization of the region irradiated by focused laser will produce instant high temperature for absorbing the laser energy, which leads the diseased tissues of the cervical mucosal to be vaporized and carbonized. And a coking surface will be formed after the diseased tissue is removed, which will seal the capillaries to prevent bleeding and bacterial infection. This is a common treatment of cervical mucosal lesion.

Although Philip knife and conventional $CO_2$ laser have been widely used in the treatment of cervical diseases, there still exist the following shortcomings: 1. Both of them are non-visual operations, which lead the surgeon workload intensity during treatment courses; 2. The treatment course depends on doctor's eyesight and experience, so they have highly requirement on specialty and more complex treatment courses; 3. Surgery time is longer, for example, the surgery time of Philip knife treatment is 10 to 30 minutes, and the surgery time of $CO_2$ laser treatment is 5 to 10 minutes, the longer surgery time will further increases surgeon workload, and less patients could be treated in a period; 4. The treatment course could not be recorded by pictures, video or other appropriate forms, which is adverse to following works.

SUMMARY OF THE INVENTION

In order to solve the above technical problems, the present invention provides a visual fractional laser instrument, comprising:

a positioning cannula, the positioning cannula being a hollow tube with openings at both ends and used to locate a lesion site and define a path of the laser;

a beam combiner component, the beam combiner component being a hollow tube with openings at both ends, and a side of the beam combiner component being provided with a side opening, wherein one end of the beam combiner component is connected to one end of the positioning cannula;

a camera connected to the beam combiner component by the side opening to image the lesion site;

a laser scanning component connected to another end of the beam combiner component for generating a laser beam used to scan the lesion site based on the image of the lesion site; and a control system connected to the laser scanning component and the camera, respectively, for receiving a lesion image data generated by the camera and controlling the laser scanning component to generate the laser beam for operation based on the lesion image data.

Further, the laser scanning component comprises:

a laser generator connected to the control system to generate the laser beam based on a control signal generated by the control system; and a fractional laser scanner, a laser exit port of which is connected to the beam combiner component and a laser entrance port of which is connected to the laser generator, and the fractional laser scanner is connected to the control system to receive the laser beam and change a path of the laser beam based on a control signal generated by the control system.

Further, a spot of the laser beam formed on the lesion site has a diameter between 0.1 mm and 0.3 mm.

Alternatively, the laser generator is a $CO_2$ laser generator, a semiconductor laser, a fiber laser, or a solid-state laser.

Still further, the beam combiner component comprises:

a beam combiner housing with a cylindrical structure having openings at both ends and a side opening provided on the side, and one end of the beam combiner housing being connected to the one end of the positioning cannula, the other end of the beam combiner housing being connected to the laser scanning component;

a focusing lens provided inside the beam combiner housing, and disposed close to the another end of the beam combiner housing and perpendicular to a side of the beam combiner housing; and a beam combiner mirror provided inside the beam combiner housing, and wherein an angle between the beam combiner mirror and the side of the beam combiner housing is 45°.

Further, the laser beam generated by the laser scanning component can be focused at a port of another end of the positioning cannula through the focusing lens.

Alternatively, the visual fractional laser instrument further includes a total reflection mirror that is provided outside of the beam combiner housing and in parallel with the beam combiner mirror, and endpoints of the total reflection mirror and endpoints of the beam combiner, which are corresponding to the side opening of the beam combiner housing, are in a same line.

Alternatively, the camera is a CCD camera, and the camera has a focusing lens.

Further, a suction exhaust port is provided on a side wall of the positioning cannula, the suction exhaust port is communicated with inside of the positioning cannula to discharge smoke generated during the treatment.

Further, the control system is connected to an external data storage, a variety of treatment information data generated during the treatment can be saved in the external data storage in real time.

The fractional laser instrument according to the present invention has the following technical effects: 1. the fractional laser instrument can display images of the lesion site of the cervix with high quality on a computer screen, implementing visible operation; 2. the operation of the fractional laser instrument is simple and easy to learn, so doctors can use it in clinical office after simple training, which will extend scope of clinical application and treatment of patients; 3. the visual fractional laser instrument allows doctor manually draw vector graphics or automatically generates the vector graphics by a imaging processing software through the control system based on images of the diseased region captured by the camera, thereby improving the design accuracy of operating area; 4. treating with fractional laser and performing automatically, which will reduce surgeon workload and error rate; 5. since the fractional laser has a quick scanning speed, a shallow affected area of the operation wound heat, little bleeding and quick healing, thus patient's pain is reduced; 6. treating images are transmitted to and saved in an external storage device so as to facilitate to store electronic medical records; 7. operating time can be limited in 20 s-60 s, which further reduces surgeon workload and improves the working efficiency.

BRIEF DESCRIPTION OF THE DRAWINGS

FIG. 1 is a schematic diagram of a visual fractional laser instrument according to an illustrative embodiment of the present invention.

DETAILED DESCRIPTION OF THE EMBODIMENTS

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

With reference to FIG. 1, a visual fractional laser instrument according to an embodiment of the present invention comprises a positioning cannula 1, a beam combiner component 2, a camera 3, a laser scanning component and a control system 4. One end of the positioning cannula 1 is connected to one end of the beam combiner component 2. The laser scanning component 6 is connected to another end of the beam combiner component 2. The camera 3 is fitted with a side opening 2-1 provided on a side of the beam combiner component, and the laser scanning component 6 and the camera 3 are connected to the control system 4, respectively. The control system 4 can control the laser scanning component to generate focused laser beams based on an image of the lesion site captured by the camera 3 so as to irradiate the lesion site for treatment.

The positioning cannula 1 is a hollow tube with openings at both ends. During a visual fractional laser treatment, the positioning cannula 1 is used to locate a lesion site of a patient for the treatment of the visual fractional laser instrument. Further, the positioning cannula 1 defines a laser path of the laser beam so that the laser path of laser is defined in a range limited by the positioning cannula. The positioning cannula 1 is a disposable medical instrument in order to ensure safety of therapy and prevent cross infection.

The beam combiner component 2 is a hollow tube with openings at both ends, and a side opening is provided on a side of the beam combiner component. One end of the beam combiner component 2 is connected to one end of the positioning cannula 1, and the side opening of the beam combiner component 2 is fitted with the camera 3, thereby transferring the image of the lesion site to the camera 3 and further to the control system 4.

The camera 3 is connected to the beam combiner component 2 through the side opening of the beam combiner component 2 so as to image the lesion site and send the image to the control system 4. The control system 4 processes the image by using an image processing software installed in it to generate a vector graphics of scanning area for the laser treatment. Compared with the conventional treatment methods, the visual fractional laser instrument allows a doctor manually draw the vector graphics or automatically generate the vector graphics by the imaging processing software based on the image of the diseased region, thereby improving accuracy and safety of the operation. Further, the disease lesion and the progress of the operation are presented to the doctor visually and real-timely, so as to facilitate the doctor to find out the situation of the disease and treatment.

Preferably, the camera 3 is a CCD camera, and the camera 3 has a focusing lens 31. The CCD camera may convert an optical image of the disease area to a digital signal, and further transfer the digital signal to the control system 4 for further processing. The focusing lens 31 can help the camera focusing to improve imaging clarity of the disease area.

The laser scanning component is connected to another end of the beam combiner component 2, which is opposite to the one end of the beam combiner component connected to the positioning cannula, so as to generate laser beams used to scan the lesion site based on the image of the lesion site. The control system 4 generates the vector graphics of the lesion site after receiving the image of the lesion site transmitted by the camera 3. The doctor may set laser scanning motion parameters in the control system 4 according to the vector graphics, then the control system 4 can send a control signal to the laser scanning component according to the set parameters, wherein the control signal is used to control the laser scanning component to generate the laser for scanning the lesion site. The above laser scanning parameters set by the doctor may comprise a laser output power, a laser scanning speed, a laser scanning path and fill distance and an angle, and the same. The depth and extent of laser ablation may be changed by varying the laser output power, scanning speed, scanning times, and setting the scanning range, to meet clinical needs of different situations. The laser scanning component generates a required laser dose based on the image of the lesion site and transmits the laser dose to the lesion site. That will significantly shorten the operation time, reduce the doctor's workload, and reduce patient's bleeding and pain during the operation.

The control system 4 is connected to the laser scanning component and the camera 3, respectively. The control system 4 may receive lesion image data generated by the camera 3 to display the lesion image for the doctor. The doctor may set the laser scanning parameters according to the lesion image. Meanwhile, the control system 4 sends a control command to the laser scanning component based on the lesion image data to generate laser and finish the laser scanning process. Preferably, the control system 4 is connected to the laser scanning component and the camera 3 via cables, respectively.

Preferably, the control system 4 is connected to an external data storage (not shown in the drawing) to store treatment information data generated during the operation in the external data storage in real time. The connection way between the control system 4 and the external data storage may be a wireless connection or a wired connection. The treatment information data may be the laser scanning motion parameters set by the doctor during the treatment, or pictures or video of the lesion site during the treatment, and the same. However, those skilled in the art should understand that the laser scanning motion parameters are not limited to these. Saving the treatment data in an external storage device may provide help to case study and evidence to possible medical disputes.

Further, the laser scanning component may include a laser generator 5 and a fractional laser scanner 6. The laser generator 5 is connected to the control system 4, and generates the laser beam according to the laser scanning motion parameters (i.e., a control signal) set by an operator in the control system 4 and sends the laser beam to the fractional laser scanner 6. A laser exit port of the fractional laser scanner 6 is connected to the beam combiner component 2 and a laser entrance port of the fractional laser scanner 6 is connected to the laser generator 5 to receive the laser beam emitted by the laser generator 5. Meanwhile, the fractional laser scanner 6 is connected with the control system 4, and changes a path of the laser beam transmitted from the laser generator 5 according to the control signal from the control system 4. The laser for scanning the lesion site sequentially passes through the beam combiner component 2 and the positioning cannula 1, and reaches the lesion site and treats it. In an embodiment, the laser for scanning the lesion may form a spot on the lesion with a diameter between 0.1 mm and 0.3 mm. Preferably, the laser generator 5 and the fractional laser scanner 6 are connected to the control system 4 via cables, respectively.

Preferably, the above laser generator may be a $CO_2$ laser generator, a semiconductor laser, a fiber laser, or a solid-state laser. The $CO_2$ laser generator targets at water. When the diameter of the laser beam is adjusted to hundreds of micrometers, the laser beam can penetrate cuticle tissue and enter dermal tissue under a high energy density. As this kind of laser has a better absorbent to water, tissues of the lesion irradiated by the laser instantly generates a very high temperature due to absorption of laser energy, which will remove the lesion tissue by vaporation. Although the laser generators listed above are preferably applied in the laser instrument of the present invention, the laser instrument of the present invention is not limited to use the above laser generator and any common laser generator in the art may be used.

Further, the beam combiner component 2 comprises a beam combiner housing 21, a focusing mirror 22 and a beam combiner mirror 23, wherein the focusing mirror 22 and the beam combiner mirror 23 are disposed inside the beam combiner housing 21. The beam combiner housing 21 has a cylindrical structure with both open ends and a side opening formed on the side. One end of the beam combiner housing 21 is connected to the one end of the positioning cannula 1, the other end of the beam combiner housing 21 is connected to the laser scanning component, so as to function to support the focusing mirror 22 and the beam combiner mirror 23. The focusing mirror 22 is provided inside the beam combiner housing 21, and is located close to the another end of the beam combiner housing 21 connected to the beam-combination mirror 23 and perpendicular to the side of the beam combiner housing 21. A $CO_2$ laser emitted by the laser scanning component firstly passes through the focusing lens 22, which may focus the $CO_2$ laser, thereby increasing power density of the laser beam affected on the lesion. The beam combiner mirror 23 is provided inside the beam combiner housing 21, and an angle between the beam combiner mirror 23 and the beam combiner housing 21 is 45°. The beam combiner mirror 23 allows almost all of the $CO_2$ lasers to penetrate and irradiate the lesion site while reflecting imaging beams to the camera 3 so as to assist the imaging step of the lesion site, so that the entire structure of the beam combiner component 2 is simple and easy to be molded.

Preferably, the laser beam generated by the laser scanning component may be focused at a port of the other end (i.e., the end closer to the lesion) of the positioning cannula 1 via the focusing lens 22. The length of the positioning cannula 1 corresponds to the focal length of the focusing lens 22, so that the laser beam passing through the focusing lens 22 is focused at the port of the end of the positioning cannula 1, which contacts with the lesion site, i.e., focusing the laser beam accurately at the lesion site. This can save the doctor's work of frequently adjusting the distance between the laser head and the lesion to focus the laser beam, so that requirements of medical experience and the doctor's work intensity are reduced.

According to an embodiment, as shown in FIG. 1, the visual fractional laser instrument according to an embodiment of the present invention further includes a total reflection mirror 7, which is provided outside of the beam combiner housing 21 and is parallel to the beam combiner mirror 23. Further, the endpoints of the total reflection mirror 7 and the endpoints of the beam-combination mirror 23, which are corresponding to the side opening of the beam combiner housing 21, are in the same line. That is to say, an angle between the total reflection mirror 7 and the side of the beam combiner housing 21 is also 45°. The imaging beam of the lesion site is fully reflected to the total reflection mirror 7 on the beam combiner mirror 23, and then the total reflection mirror 7 fully reflects the imaging beam to the field of view of the camera 3. The camera 3 captures the imaging beam and sends the diseased imaging data to the control system 4 through cables, thus completes collection of the lesion information.

Further, a suction exhaust port 8 is provided on the side wall of the positioning cannula 1. The suction exhaust port 8 is communicated with inside of the positioning cannula 1 and is connected with an external suction machine (not shown in FIG. 1) or other power sources (not shown in FIG. 1) to discharge the smoke generated during the treatment. Cell tissues of the lesion site instantly generate a high temperature, which is higher than thousands of degrees, by the irradiation of the focused $CO_2$ laser. This leads the cell tissues to be vaporized quickly so as to form a strong smoke, therefore the smoke may be removed from the operation room by disposing the suction exhaust port 8 so as to maintain a healthy treatment environment.

The operation process of the visual fractional laser instrument according to the embodiments of the present invention are described as follows: the positioning cannula 1 is connected to the beam combiner component 2 and the camera 3, and the positioning cannula 1 is inserted into a vaginal speculum to reach cervix; the camera 3 images the lesion site and transmits a imaging data to the control system 4; the control system 4 generates a vector graphics of the area to be treated according to the data transmitted by the camera 3, and then the doctor sets laser scanning motion parameters for the generated vector graphics according to the lesion degree; after the parameters are set, the doctor may start a laser emission switch (a manual button or a pedal switch); the control system 4 sends a control signal to control the laser generator 5 to generate a laser beam, which is to be emitted to the fractional laser scanner 6; the control system 4 sends a control signal to the fractional laser scanner 6, so as to control the fractional laser scanner 6 to change the path of the laser beam based on the laser scanning motion parameters set by the doctor to generate a fractional laser, and send the fractional laser to the lesion site for treatment.

The visual fractional laser instrument according to the embodiments of the present invention can be used in the treatment of cervical intraepithelial neoplasia (CIN) which has been diagnosed, particularly in the treatment of CIN II-III, chronic cervicitis, atypical cervical hyperplasia, and high risk HPV infection in the cervix, and other gynecological diseases. It should be understand by those skilled in the art that the field of application of the visual fractional laser instrument is not limited to the above mentioned diseases.

Two typical examples of treatment with a conventional $CO_2$ laser treatment instrument and a visual fractional laser treatment instrument according to an embodiment of the present invention will be described below.

EXAMPLE 1 treatment of chromic cervicitis using a conventional $CO_2$ laser treatment instrument and the visual fractional laser treatment instrument, respectively:

Treatment with the conventional $CO_2$ laser treatment instrument: a patient with bladder lithotomy position, routinely sterilizing vulva and vagina. The $CO_2$ laser treatment instrument is selected to have a power of 20~30 W, a spot diameter of 0.3~0.5 mm, and a distance of 5~10 cm from the cut to the cervix. The surgeon holds a handle of the instrument and aims at the lesion site by eyes to burn the lesion site point-by-point. The burning range should excess about 2 mm beyond the edge of the lesion site, the rotating speed should be appropriate, and the slower the burning speed is with the deeper burning. In the event of bleeding, pressing or laser beam could be used to stop bleeding. The burning to the cervix should not be too deep, otherwise, this may cause cervical adhesions or stenosis. The duration of this procedure is about 20 minutes.

Treatment with the visual fractional $CO_2$ laser instrument: conventional disinfection. The $CO_2$ laser instrument is selected to have a power of 30~50 W and a spot diameter of 0.1~0.3 mm. A treatment range is selected by images captured by the camera and the lesion site is automatically performed fractional scanning and burning. The burning range should excess about 2 mm beyond the edge of the lesion site. The laser power, scan mode and scan speed can be chosen as requirement, and the burning depth can be adjusted by changing the laser power and scan speed.

EXAMPLE 2

Cervical Atypical Hyperplasia and High Risk of Cervical HPV Infection

The common $CO_2$ laser treatment is only applicable to squamous epithelial dysplasia. A $CO_2$ laser with a power of 20~30 W evenly scans the lesion site of cervix from outside to inside and from posterior lip to anterior lip to vaporize the lesion site. The depth around the cervix site is 0.5~1 cm, and the vaporizing depth around the cervix is relatively shallow, so that the appearance of the section presents a conical shape.

Treatment with the visual fractional $CO_2$ laser instrument: routinely disinfect; determining the cervix has infected high-risk HPV and squamous epithelial dysplasia by the cervical smear. A $CO_2$ laser instrument is selected to have a power of 30~50 W and a spot diameter of 0.2~0.3 mm. A distance from the cut to the cervix is 20 cm. A treating area is selected according to the images captured by the camera. The lesion site is quickly scanned and burned with the fractional laser. The laser power, scan mode and scan speed can be chose as requirement, and the burning depth and range can be adjusted by changing the laser power and scan speed and setting an area to meet different clinical demands.

Although the visual fractional laser instrument according to the present invention has been described with reference to the above preferable embodiments, the present invention is not limited thereto. Those skilled in the art will appreciate that various change, replacement and modification may be made to the embodiment without departing from the principle and spirit of present invention, and the scope of the present invention is limited solely by the appended claims and its equivalents.

The invention claimed is:

1. A visual fractional laser instrument, comprising:
   a positioning cannula, the positioning cannula being a hollow tube with openings at both a first end and a second end opposite to the first end, and configured to locate a lesion site and define a path of the laser;
   a beam combiner component, the beam combiner component being a hollow tube with openings at both ends, and a side of the beam combiner component being provided with a side opening, wherein one end of the beam combiner component is connected to the second end of the positioning cannula;
   a camera connected to the beam combiner component by the side opening to image the lesion site;
   a laser scanning component connected to another end of the beam combiner component for generating a laser beam used to scan the lesion site based on the image of the lesion site; and
   a control system connected to the laser scanning component and the camera, respectively, for receiving a lesion image data generated by the camera and controlling the laser scanning component to generate the laser beam based on the lesion image data,
   wherein, the laser scanning component comprises:
   a laser generator connected to the control system to generate the laser beam based on a control signal generated by the control system; and
   a fractional laser scanner, a laser exit port of which is connected to the beam combiner component and a laser entrance port of which is connected to the laser generator, and the fractional laser scanner being connected to the control system to receive the laser beam and change a path of the laser beam based on a control signal generated by the control system,
   wherein, the beam combiner component comprises:
   a beam combiner housing with a cylindrical structure having openings at both ends and a side opening provided on the side, and one end of the beam combiner housing being connected to the second end of the positioning cannula, the other end of the beam combiner housing being connected to the laser scanning component;

a focusing lens provided inside the beam combiner housing, and disposed close to the other end of the beam combiner housing and perpendicular to a side of the beam combiner housing; and a beam combiner mirror provided inside the beam combiner housing, and wherein an angle between the beam combiner mirror and the side of the beam combiner housing is 45°, and wherein, a length of the positioning cannula between the first end and the second end corresponds to a focal length of the focusing lens, so that the laser beam generated by the laser scanning component is focused at a port of the first end of the positioning cannula through the focusing lens, and wherein the visual fractional laser instrument further includes a total reflection mirror that is provided outside of the beam combiner housing and in parallel to the beam combiner mirror.

2. The visual fractional laser instrument of claim 1, wherein, a spot of the laser beam formed on the lesion site has a diameter between 0.1 mm and 0.3 mm.

3. The visual fractional laser instrument of claim 1, wherein, the laser generator is a CO2 laser generator, a semiconductor laser, a fiber laser, or a solid-state laser.

4. The visual fractional laser instrument of claim 1, wherein, endpoints of the total reflection mirror and endpoints of the beam combiner mirror, which are corresponding to respective end points of the side opening of the beam combiner housing, are in a same line, wherein an angle between the total reflection mirror and the side of beam combiner housing is also 45 degree.

5. The visual fractional laser instrument of claim 1, wherein, the camera is a CCD camera, and the camera has a focusing lens.

6. The visual fractional laser instrument of claim 1, wherein, a suction exhaust port is provided on a side wall of the positioning cannula, the suction exhaust port is communicated with inside of the positioning cannula to discharge smoke generated during a treatment.

7. The visual fractional laser instrument of claim 1, wherein, the control system is connected to an external data storage, a variety of treatment information data generated during a treatment are saved in the external data storage in real time.

8. A method of treating gynecological diseases utilizing the visual fractional laser instrument of claim 1, the method comprising:

inserting the positioning cannula into a vaginal speculum of a patient, the positioning cannula contacting the lesion site of the patient;

imaging the lesion site by the camera and transmitting the lesion imaging data to the control system;

generating the laser beam by the laser generator according to the control signal generated by the control system;

generating the fractional laser by the fractional laser scanner to change the path of the laser beam; and focusing the fractional laser by the focusing lens to the lesion site at the first end of the positioning cannula.

* * * * *